United States Patent [19]

Oiwa

[11] 4,180,071
[45] Dec. 25, 1979

[54] DEVICE FOR WITHDRAWING INJECTION SOLUTION

[76] Inventor: Shigeo Oiwa, No. 10-6, 2-chome, Nishimaiko, Tarumi-ku, Kobe, Japan

[21] Appl. No.: 835,955

[22] Filed: Sep. 23, 1977

[30] Foreign Application Priority Data

Oct. 1, 1976 [JP] Japan ................................ 51-118755

[51] Int. Cl.² ............................................ A61M 5/00
[52] U.S. Cl. ................................. 128/218 N; 128/221
[58] Field of Search ............... 128/218 N, 218 R, 221, 128/215, 214 R, 184

[56] References Cited

U.S. PATENT DOCUMENTS

| | | | |
|---|---|---|---|
| 1,830,453 | 11/1931 | Wassmer | 128/184 X |
| 2,689,564 | 9/1954 | Adams et al. | 128/214 R |
| 2,827,081 | 3/1958 | Little | 128/214 R X |
| 2,972,991 | 2/1961 | Burke | 128/218 N |

Primary Examiner—John D. Yasko
Attorney, Agent, or Firm—Oblon, Fisher, Spivak, McClelland & Maier

[57] ABSTRACT

A device for withdrawing an injection solution wherein fine glass fragments can be readily filtered off for removal. The device comprises a tube which can cover an injection needle and has one end intimately fitted to the base portion of the needle and the other end packed with a filter medium. Because the interior of the tube is subjected to reduced pressure when the needle withdraws the injection solution from an ampule with the latter end immersed in the solution, the whole solution is withdrawn from the ampule through the filter medium.

4 Claims, 5 Drawing Figures

DEVICE FOR WITHDRAWING INJECTION SOLUTION

BACKGROUND OF THE INVENTION

This invention relates to a device for withdrawing an injection solution, and more particularly to a device for withdrawing an injection solution in the form of a tube having one end intimately fittable to the base portion of an injection needle and the other end packed with a filter medium.

When solution-containing ampules are cut at the neck to give injections, many fine fragments of glass formed ingress into the solution and are introduced into the body along with the solution. Ever since this problem was raised in the field of medication, many devices including various adaptors have been proposed in an attempt to render the injection solution free from glass fragments, but none of these devices are satisfactory because some are complex in construction and others are inconvenient to use.

SUMMARY OF THE INVENTION

Accordingly, one object of this invention is to provide a novel device for removing glass fragments from an injection solution.

It is another object of this invention to provide such a device which is simple in structure, convenient to use and capable of removing any glass fragments.

In the present invention fine glass fragments can be readily filtered off for removal by the use of a tube covering the injection needle and having one end intimately fitted to the base portion of the needle and the other end packed with a filter medium, because the interior of the tube is subjected to reduce pressure when the needle withdraws the injection solution from an ampule with the latter end immersed in the solution, permitting the whole solution to be withdrawn from the ampule through the filter medium.

BRIEF DESCRIPTION OF THE DRAWINGS

This invention will be described below with reference to the drawings showing embodiments.

DESCRIPTION OF THE PREFERRED EMBODIMENT

Figure 1:
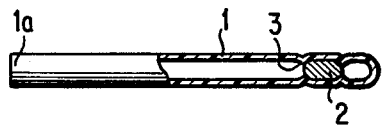
FIG. 1 is a plan view partly broken away and showing an injection withdrawing device embodying this invention.
Figure 2:
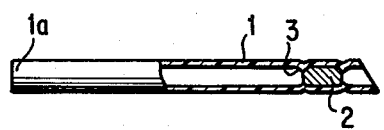
FIG. 2 is a side elevation partly broken away and showing the same.
Figure 3:
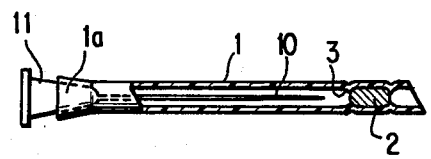
FIGS. 3 and 4 are side elevations partly broken away and showing the solution withdrawing device of FIGS. 1 and 2 in its different modes of application.
Figure 4:
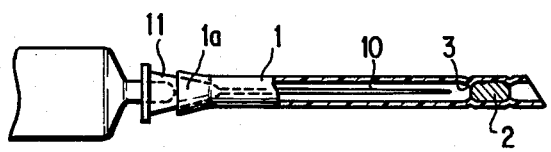
Figure 5:
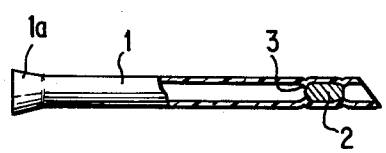
FIG. 5 is a side elevation partly broken away to show another embodiment of the solution withdrawing device according to this invention.

Referring now to the drawings, wherein like reference numerals designate identical or corresponding parts, and more particularly to FIG. 1 thereof, a tube 1 is usually made of soft or hard synthetic resin or light metal such as aluminum. The tube 1 has such a length that when the tube is intimately fitted at its one end to the base portion 11 of an injection needle 10, the filter medium 2 packed in the other end, i.e. the front end, of the tube will be positioned slightly to the front of the tip of the needle 10. The diameter of tube 1 may be so dimensioned as to freely accommodate the needle 10 therein; usually it is 2 to 3 mm in inside diameter. Preferably, the tube 1 has an oblique front end extremity. This will eliminate the difficulty to be otherwise encountered in withdrawing the solution owing to the intimate contact of the tube front end with the inner surface of the ampule. The tube 1, when made of flexible soft synthetic resin, can be intimately fitted to the base portion 11 of the needle merely by being forced into fitting contact therewith, so that the tube need not be provided with a particular portion 1a intimately fittable to the needle base portion 11. However, when the tube 1 is made of non-flexible material such as hard synthetic resin, the tube may be formed with a fitting portion 1a shown in FIG. 5 and conforming to the shape of the needle base portion 11.

Preferably the base portion 11 of the needle is circular in cross section and tapered to render the tube 1 easily and completely fittable to the base portion is in intimate contact therewith.

Although not shown, the needle base portion 11 may be provided on its outer periphery with a suitable engaging projection which will then insure intimate contact between the tube 1 and the needle base portion 11 more effectively.

Useful but not limitative examples of the filter medium 2 to be packed in the front end of the tube 1 are usually polyurethane foam and a mass of fine fibers as a polyester, polypropylene, polyamide or the like. The thickness of the layer of the filter medium 2 is suitably determined depending on the material thereof, the density of the filter medium 2 as packed in the tube 1, etc. The density of the filter medium 2 is suitably adjustable in accordance with the material or the amount of the filter medium to be used. The density of the filter medium 2 is adjustable also after the filter medium 2 has been packed in the tube 1 for example by shrinking part of the peripheral wall of the filter medium 2 through hot pressing or by permanently deforming the same by cold pressing. It is preferable that the filter medium 2 eventually have a multiplicity of pores of a 3 to $5\mu$ in diameter.

The filter medium 2 is packed into the tube 1 usually by being forced into the tube 1 from its front end. To pack the filter medium 2 in a specified position, the tube may be provided with an internal projection 3 at each of the opposite ends of the portion where the filter medium 2 is to be positioned so as to render the inserted filter medium somewhat retainable by the projection 3. This is desirable since the filter medium 2 can be retained in the tube 1 against displacement during transport or use.

The solution withdrawing device of this invention has the construction described above and is used in the following manner. The fitting portion 1a of the tube 1 is suitably intimately fitted to the base portion 11 of the injection needle 11, the front end of the tube is then immersed in the solution in an ampule, and the solution is withdrawn into the barrel of the syringe in the usual fashion. At this time, a vacuum is produced within the tube 1, causing the solution to flow into the needle through the filter medium 2, whereby any glass fragments, if contained in the ampule, will be filtered off and removed. Upon completion of the withdrawal of the solution, the tube 1 is removed from the needle base portion 11 to give an injection in the usual manner.

The solution withdrawing device of this invention has the advantages of being inexpensive to make because of its simple construction, permitting the withdrawal of the solution with ease because the filtration is effected over a relatively large area, and being capable of completely removing foreign matter such as glass fragments because the solution is withdrawn wholly through the filter medium 2. The present device is useful, therefore.

Obviously, many modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for withdrawing an injection solution comprising:
   a tube, said tube having one open end which is adapted to be intimately fitted to the base portion of an injection needle and another open end which is oblique;
   a filter medium packed into said tube adjacent said other end, said filter medium having pores of 3 to 5μ in diameter;
   two internal projections on said tube, one adjacent either end of said filter medium whereby said projections maintain the position of said filter medium within said tube; and
   the portion of said tube surrounding said filter medium having a lesser diameter than the remainder of said tube, said lesser diameter increasing the density of said filter medium.

2. The device of claim 1 wherein said filter medium is polyurethane foam and fibers made from one from the group consisting of polyester, polypropylene and polyamide.

3. The device of claim 1 wherein said reduced diameter is provided by hot pressing.

4. The device of claim 1 wherein said reduced diameter is a permanent deformation produced by cold pressing.

* * * * *